United States Patent [19]
Cox et al.

[11] Patent Number: 6,140,129
[45] Date of Patent: Oct. 31, 2000

[54] CHROMOSOMAL TARGETING IN BACTERIA USING FLP RECOMBINASE

[75] Inventors: Michael M. Cox, Oregon; Elizabeth A. Wood, Madison, both of Wis.; Li-chun Huang, Cupertina, Calif.

[73] Assignee: Wisconsin Alumni Research Foundation, Madison, Wis.

[21] Appl. No.: 09/154,429

[22] Filed: Sep. 16, 1998

Related U.S. Application Data

[60] Provisional application No. 60/059,128, Sep. 17, 1997.

[51] Int. Cl.[7] .................................................. C12N 15/74
[52] U.S. Cl. ...................... 435/477; 435/91.4; 435/320.1
[58] Field of Search ............................... 435/477, 320.1, 435/91.4

[56] References Cited

U.S. PATENT DOCUMENTS

| | | | |
|---|---|---|---|
| 5,851,808 | 12/1998 | Elledge et al. | 435/91.4 |
| 5,888,732 | 3/1999 | Hartley et al. | 435/6 |

OTHER PUBLICATIONS

Yasuda et al. Journal of Bacteriology. vol. 154(3), pp. 1153–1161, Jun. 1983.

Rao et al. Gene. vol. 7, pp. 79–82, 1979.

Baubonis, W., and Sauer, B., "Genomic targeting with purified Cre recombinase," *Nucleic Acids Res.*, 21:2025–2029 (1993).

Bayley, C.C., Morgan, M., Dale, E.C. and Ow, D.W., "Exchange of gene activity in transgenic plants catalyzed by the Cre–lox site–specific recombination system," *Plant. Mol. Biol.,* 18:353–361 (1992).

Bernet, A., Sabatier, S., Picketts, D.J., Ouazana, R., Morlé, F., Higgs, D.R. and Godet, J., "Targeted Inactivation of the Major Positive Regulatory Element (HS–40) of the Human α–Globin Gene Locus," *Blood,* 86:1202–1211 (1995).

Bruckner, R.C. and Cox, M.M., "Specific Contacts between the FLP Protein of the Yeast 2–Micron Plasmid and Its Recombination Site," *J. Biol. Chem.,* 261:11798–11807 (1986).

Cherepanov, P.P., and Wackernagel, W., "Gene disruption in *Escherichia coli:* Tc$^R$ and Km$^R$ cassettes with the option of Flp–catalyzed excision of the antibiotic–resistance determinant," *Gene,* 158:9–14 (1995).

Cox, M.M., "The FLP protein of the yeast 2–μm plasmid: Expression of a eukaryotic genetic recombination system in *Escherichia coli,*" *Proc. Natl. Acad. Sci. USA,* 80:4223–4227 (1983).

DiSanto, J.P., Müller, W., Guy–Grand, D., Fischer, A., and Rajewsky, K., "Lymphoid development in mice with a targeted deletion of the interleukin 2 receptor γ chain," *Proc. Natl. Acad. Sci. USA,* 92:377–381 (1995).

Fiering, S., Kim, C.G., Epner, E.M., and Groudine, M., "An 'in–out' strategy using gene targeting and FLP recombinase for the functional dissection of complex DNA regulatory elements: Analysis of the β–globin locus control region," *Proc. Natl. Acad. Sci. USA,* 90:8469–8473 (1993).

Fiering, S., Epner, E., Robinson, K., Zhuang, Y., Telling, A., Hu, M., Martin, D.I.K., Enver, T., Ley, T.J., and Groudine, M., "Targeted deletion of 5'HS2 of the murine β–globin LCR reveals that it is not essential for proper regulation of the β–globin locus," *Genes & Dev.,* 9:2203–2213 (1995).

Fukushige, S. and Sauer, B., "Genomic targeting with a positive–selection lox integration vector allows highly reproducible gene expression in mammalian cells," *Proc. Natl. Acad. Sci. USA,* 89:7905–7909 (1992).

Fuse, T., Kodama, H., Hayashida, N., Shinozaki, K., Nishimura, M. and Iba, K., "A novel Ti–plasmid–convertible λ phage vector system suitable for gene isolation by genetic complementation of *Arabidopsis thaliana* mutants," *Plant J.,* 7:849–856 (1995).

Gage, P.J., Sauer, B., Levin, M. and Glorioso, J.C., "A Cell–Free Recombination System for Site–Specific Integration of Multigenic Shuttle Plasmids into the Herpes Simplex Virus Type 1 Genome," *J. Virol.,* 66:5509–5515 (1992).

Golic, K.G. and Lindquist, S., "The FLP Recombinase of Yeast Catalyzed Site–Specific Recombination in the Drosophila Genome," *Cell,* 59:499–509 (1989).

Golic, K.G., "Local Transposition of P Elements in *Drosophila melanogaster* and Recombination Between Duplicated Elements Using a Site–Specific Recombinase," *Genetics,* 137:551–563 (1994).

Gu, H., Zou, Y.–R., and Rajewsky, K., "Independent Control of Immunoglobulin Switch Recombination at Individual Switch Regions Evidenced Through Cre–loxP–Mediated Gene Targeting," *Cell,* 73:1155–1164 (1993).

Huang, L.–C., Wood, E.A., and Cox, Michael M., "A bacterial model system for chromosomal targeting," *Nucleic Acids Research,* 19:443–448 (1991).

Huang, L.–C., Wood, E.A., and Cox, Michael M., "Convenient and Reversible Site–Specific Targeting of Exogenous DNA into a Bacterial Chromosome by Use of the FLP Recombinase: the Flirt System," *J. Bacteriol.,* vol. 179:6076–6083 (1997).

(List continued on next page.)

*Primary Examiner*—Remy Yucel
*Attorney, Agent, or Firm*—Quarles & Brady LLP

[57] ABSTRACT

A method of introducing exogenous cloned DNA into a bacterial chromosome of a bacteria in which the transposon Tn5 and the FLP recombinase are functional in vivo is disclosed. In one embodiment, the method comprises the steps of: (a) introducing FLP recombination target sites (FRTs) permanently at random locations in a bacterial chromosome using a plasmid vector that contains an FRT within a modified Tn5 transposon, two selectable markers, and a removable replication origin; (b) mapping the FRT introduced into the bacterial chromosome; (c) cloning exogenous DNA into a vector comprising two FRT sites, two selectable markers, and a removable replication origin; (d) removing the replication origin in the vector of step (c); (e) introducing the altered plasmid vector into bacterial cells, wherein the bacteria cells comprise a functional FLP recombinase; and (f) obtaining targeted integrants.

11 Claims, 6 Drawing Sheets

OTHER PUBLICATIONS

Lakso, M., Sauer, B., Mosinger, Jr., B., Lee, E.J., Manning R.W., Yu, S.–H., Mulder, K.L., and Westphal, H., "Targeted oncogene activation by site–specific recombination in transgenic mice," *Proc. Natl. Acad. Sci. USA,* 89:6232–6236 (1992).

Lakso, M., Pichel, J.G., Gorman, J.R., Sauer, B., Okamoto, Y., Lee, E., Alt, F.W. and Westphal, H., "Efficient in vivo manipulation of mouse genomic sequences at the zygote stage," *Proc. Natl. Acad. Sci. USA,* 93:5860–5865 (1996).

Leslie, N.R.A., and Sherratt, D.J., "Site–specific recombination in the replication terminus region of *Escherichia coli*: functional replacement of dif," *EMBO J.,* 14:1561–1570 (1995).

Marshall, Eliot, "The Mouse That Prompted a Roar," *Science,* 277:24–25, Jul. 4, 1997.

Medberry, S.L., Dale, E., Qin, M., and Ow, D.W., "Intra–chromosomal rearrangements generated by Cre–lox site–specific recombination," *Nucleic Aicds Res.,* 23:485–490 (1995).

Meyer–Leon, L., Huang, L.–C., Umlauf, S.W., Cox, M.M. and Inman, R.B., "Holliday Intermediates and Reaction By–Products in FLP Protein–Promoted Site–Specific Recombination," *Mol. Cell. Biol.,* vol. 8:3784–3796 (1988).

Meyer–Leon, L., Inman, R.B., and Cox, M.M., "Characterization of Holliday Structures in FLP Protein–Promoted Site–Specific Recombination," *Mol. Cell. Biol.,* 10:235–242 (1990).

Morris, A.C., Schaub, T.L., and James, A.A., "FLP–mediated recombination in the vector mosquito *Aedes aegypti*," *Nucleic Acids Res.,* 19:5895–5900 (1991).

O'Gorman, S., Fox, D.T., and Wahl, G.M., "Recombinase–Mediated Gene Activation and Site–Specific Integration in Mammalian Cells," *Science,* 251:1351–1355 (1991).

Osborne, B.I., Wirtz, U. and Baker, B., "A system for insertional mutagenesis and chromosomal rearrangement using the Ds transposon and Cre–lox," *Plant J.,* 7:687–701 (1995).

Pósfai, G., Koob, M., Hradečná, Z., Hasan, N., Filutowicz, M., and Szybalski, W., "In vivo excision and amplification of large segments of the *Escherichia coli* genome," *Nucleic Acids Res.,* 22:2392–2398 (1994).

Qian, X. and Cox, M.M., "Asymmetry in active complexes of FLP recombinase," *Genes & Development,* 9:2053–2064, Cold Spring Harbor Laboratory Press (1995).

Qin, M., Lee, E., Zankel, T., and Ow, D.W., "Site–specific cleavage of chromosomes in vitro through Cre–lox recombination," *Nucleic Acids Res.,* 23:1923–1927.

Ramírez–Solis, R., Liu, P., and Bradley, A., "Chromosome engineering in mice," *Nature,* 378:720–724 (1995).

Sauer, Brian, "Identification of Cryptic lox Sites in the Yeast Genome by Selection for Cre–mediated Chromosome Translocations that Confer Multiple Drug Resistance," *J. Mol. Biol.,* 223:911–928 (1992).

Sauer, Brian, "Manipulation of Transgenes by Site–Specific Recombination: Use of Cre Recombinase," *Methods Enzymol.,* 225:890–900 (1993).

Sauer, Brian, "Recycling Selectable Markers in Yeast," *BioTechniques,* 16:1086–1088 (1994).

Sauer, Brian, "Site–specific recombination: developments and applications," *Curr. Opin. Biotechnol.,* 5:521–527 (1994).

Senecoff, J.F., Bruckner, R.C. and Cox, M.M., "The FLP recombinase of the yeast 2–$\mu$m plasmid: Characterization of its recombination site," *Proc. Natl. Acad. Sci. USA,* 82:7270–7274 (1985).

Senecoff, J.F. and Cox, M.M., "Directionality in FLP Protein–promoted Site–specific Recombination Is Mediated by DNA–DNA Pairing," *J. Biol. Chem.,* 261:7380–7386 (1986).

Senecoff, J.F., Rossmeissl, P.J. and Cox, M.M., "DNA Recognition by the FLP Recombinase of the Yeast 2$\mu$ Plasmid, A Mutational Analysis of the FLP Binding Site," *J. Mol. Biol.* 201:405–421 (1988).

Smith, A.J.H., DeSousa, M.A., Kwabi–Addo, B., Heppell–Parton, A., Impey, H., and Rabbitts, P., "A site–directed chromosomal translocation induced in embryonic stem cells by Cre–loxP recombination," *Nat. Genet.,* 9:376–385 (1995).

Umlauf, S.W. and Cox, M.M., "The functional significance of DNA sequence structure in a site–specific genetic recombination reaction," *EMBRO J.,* vol. 7:1845–1852 (1988).

van Deursen, J., Fornerod, M., van Rees, B., and Grosveld, G., "Cre–mediated site–specific translocation between non-homologous mouse chromosomes," *Proc. Natl. Acad. Sci. USA,* 92:7376–7380 (1995).

Waite, L.L. and Cox, M.M., "A Protein Dissociation Step Limits Turnover in FLP Recombinase–mediated Site–specific Recombination," *J. Biol. Chem.,* 270:23409–23414 (1995).

Wang, P., Anton, M., Graham, F.L., and Bacchetti, S., "High Frequency Recombination Between loxP Sites in Human Chromosomes Mediated by an Adenovirus Vector Expressing Cre Recombinase," *Somatic Cell Mol. Genet.,* 21:429–441 (1995).

Xu, T., and Rubin, G.M., "Analysis of genetic mosaics in developing and adult Drosophila tissues," *Development,* 117:1223–1237 (1993).

CHROMOSOMAL TARGETING IN BACTERIA USING FLP RECOMBINASE

CROSS-REFERENCE TO RELATED APPLICATION

This application claims the priority benefit of Ser. No. 60/059,128, filed Sep. 17, 1997.

STATEMENT REGARDING FEDERALLY SPONSORED RESEARCH OR DEVELOPMENT

This invention was made with United States government support awarded by the following agencies: NIH Grant Nos.: GM37835; AI00599; GM32335; GM52725; and NSF Grant No.: MCB-9600715.

BACKGROUND OF THE INVENTION

Site-specific recombination provides a vehicle to introduce exogenous DNA, delete DNA, or rearrange DNA at specific sites in a chromosome (41). Among the site-specific recombination systems characterized to date, the FLP system of the yeast 2 micron plasmid and the Cre-lox system of bacteriophage P1 are among the most attractive for genomic manipulation because of their efficiency, simplicity, and demonstrated in vivo activity in a wide range of organisms. These systems have been used to construct specific genomic deletions and gene duplications, study gene function, promote chromosomal translocations, promote site-specific chromosome cleavage, and facilitate the construction of genomic libraries in organisms including bacteria, yeast, insects, plants, mice, and humans 2–5, 10–18, 24–26, 28, 30–35, 38–41, 44, 45, 47, 50). These studies have only begun to tap the potential of the approach.

Site-specific recombination catalyzed by the FLP and Cre recombinases occurs readily in bacterial cells (1, 5, 6, 21, 33). In principle, it could find wide application to studies of genomic structure and function as well as enhance the usefulness of *E. coli* in biotechnology. Ironically, this approach has not been exploited in bacteria as it has been in eukaryotes, although bacteria were the first non-yeast cells in which FLP-mediated recombination was demonstrated (6). Even though gene targeting in bacteria can be achieved by homologous recombination, chromosomal targeting by site-specific recombination provides a new route to stable transformation with the advantages of very high efficiency, defined reproducible insertion sites in the chromosome, and controlled reversibility.

The yeast FLP system has been studied intensively (7, 8, 22, 36). The only requirements for FLP recombination are the FLP protein and the FLP Recombination Target (FRT) sites on the DNA substrates. The minimal functional FRT site contains only 34 bp. The FLP protein can promote both inter- and intra-molecular recombination.

Previously, the inventors (Huang, et al., 1991) reported the construction of a model system in *E. coli* using the FLP recombination system for chromosomal targeting and demonstrated the effectiveness of the general approach (21). The site-specific integration was absolutely dependent upon the expression of FLP protein and the presence of FRT sites in the chromosome. In some experiments, from 1% to 10% of the exogenous DNA molecules used, introduced on a modified bacteriophage λ vector, actually found their way into a cell and were integrated into the chromosome specifically at a chromosomal FRT.

Although Huang, et al. (1991) achieved a high integration frequency in this original targeting system, there were limitations inherent to the constructs that precluded a detailed characterization as well as a convenient application of the system to bacterial cloning and genomic studies.

BRIEF SUMMARY OF THE INVENTION

We have modified previous FLP systems to provide a method that can regulate and monitor excision as well as integration, introduce FRT targets virtually anywhere in the chromosome and test a variety of additional parameters that might affect integration and/or excision. This is designated the FLIRT system, for "FLP-mediated DNA integration and rearrangement at prearranged genomic targets."

In one embodiment, the invention is a method of introducing exogenous cloned DNA into a bacterial chromosome of a bacteria in which the transposon Tn5 and the FLP recombinase are functional in vivo. The method comprises the steps of: (a) introducing at least one FLP recombination target site (FRT) permanently at random locations in a bacterial chromosome using a plasmid vector that contains an FRT within a modified Tn5 transposon, two selectable markers, and a removable replication origin; (b) mapping the introduced FRT; (c) cloning exogenous DNA into a vector comprising two FRT sites, two selectable markers, and a removable replication origin; (d) removing the replication origin in the vector of step (c); (e) introducing the altered plasmid vector into bacterial cells, wherein the bacteria cells comprise a functional FLP recombinase; and (f) obtaining targeted integrants.

In a preferred version, the bacteria is a gram negative bacteria, most preferably an *E. coli*.

In another preferred embodiment, FLP recombinase is used in step (d) to remove the origin of replication.

In another preferred embodiment, more than one FRT is introduced into the bacterial chromosome.

The present invention is also a system of plasmid constructs designed to allow very convenient use of the overall targeting scheme. One preferable plasmid comprises: (a) at least one FRT site; (b) a selectable marker located between two outside ends of transposon Tn5; and (c) a removable replication origin.

In another embodiment, the invention is a plasmid useful in cloning exogenous DNA in the method of described above. Preferably, the plasmid comprises (a) at least two FRT sites; (b) two selectable markers; (c) a removable replication origin; and (d) at least one restriction site positioned for use as a cloning site.

Most preferably, the plasmid of the present invention is selected from the group consisting of plasmid pEAW127, plasmid pEAW133, plasmid pEAW116, and plasmid pEAW1135.

It is an advantage of the present invention that a FLP cloning system is described that provides means to regulate and monitor excision and integration of a heterologous gene in a bacterial chromosome.

Other advantages, features and objects of the present invention will become apparent to one of skill in the art after review of the specification, drawings and claims.

BRIEF DESCRIPTION OF THE SEVERAL VIEWS OF THE DRAWINGS

FIG. 1A describes plasmids used to introduce FRT sites into the chromosome.

FIG. 5A is directed to introduction of FRT target #3.

BRIEF DESCRIPTION OF THE INVENTION

In General

Figure 1A:
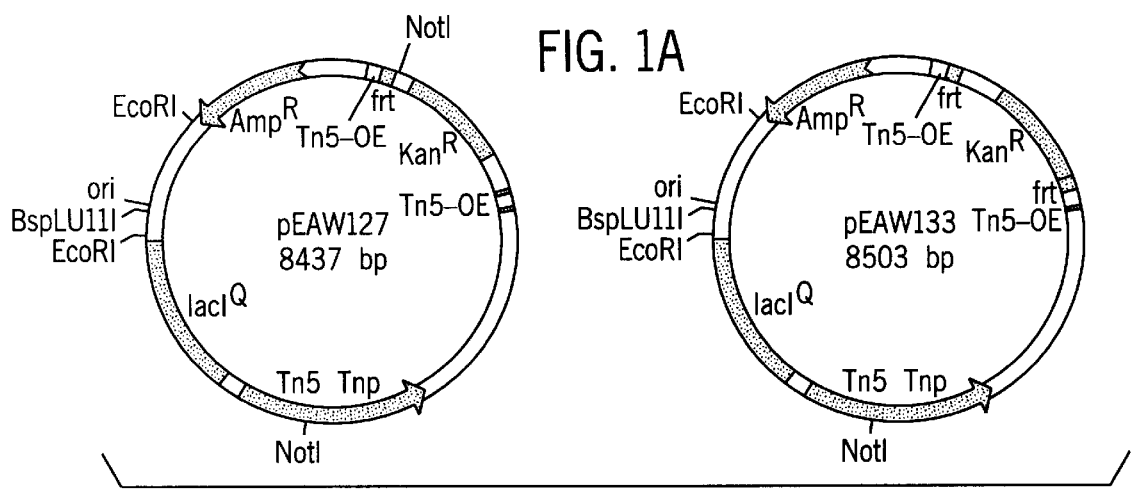
FIGS. 1A, B, and C is a diagram of the FLIRT system.

We have created a system that utilizes the FLP recombinase of yeast to introduce exogenous cloned DNA reversibly at defined locations in the *E. coli* chromosome. (This system is described in Huang, et al. (1997), hereby incorporated by reference.) Recombination target sites (FRTs) can be introduced permanently at random locations in the chromosome on a modified Tn5 transposon, now designed so that the inserted FRT can be detected and its location mapped with base pair resolution. FLP recombinase is provided as needed through the regulated expression of its gene on a plasmid. Exogenous DNA is introduced on a cloning vector that contains an FRT, selectable markers, and a replication origin designed to be deleted prior to electroporation for targeting purposes. High yields of targeted integrants are obtained, even in a recA background.

The system of the present invention permits a rapid and precise excision of the introduced DNA when needed, without destroying the cells. The efficiency of targeting appears to be affected only modestly by transcription initiation upstream of the chromosomal FRT site. With rare exceptions, FRTs introduced to the bacterial chromosome are targeted with high efficiency regardless of their location. The system should facilitate studies of bacterial genome structure and function, simplify a wide range of chromosomal cloning applications, and generally enhance the utility of *E. coli* as an experimental organism in biotechnology.

In one embodiment, the present invention is a method of introducing a foreign gene at defined locations in a bacterial chromosome. The method comprises the steps of obtaining a bacterial population, preferably an *E. coli* population, in which recombination target sites (FRTs) have been introduced permanently at random locations in the chromosome, preferably on a modified Tn5 transposon. In a most preferred form of the present invention, the inserted FRT has been detected and the location mapped.

The natural full-length Tn5 is 5818 bp in length. The plasmid we describe comprises a "modified" Tn5, which is about 1200 bp altogether. The parts necessary for a suitable vector are (1) 112 bp of the outside ends of the transposon (this is the only part of Tn5 within the plasmid section that is transferred to the bacterial chromosome), which comprises the two 56 bp segments that contain the sites that are bound by the transposase enzyme; and (2) the gene encoding the Tn5 transposase enzyme (about 1100 bp altogether). This gene is expressed and promotes the movement of the segment we are interested in from the plasmid to the chromosome. The 56 bp segments begin at the end of the transposon and extend inward for 56 bp. These segments are described in Huang, et al. (1997) and Reznikoff (1993). The plasmid itself does not replicate and hence exists only transiently in the cell. Because the transposase gene is not transferred, the transferred segment cannot come out of the chromosome once the plasmid disappears.

If one wished to use another transposon, one would need to take corresponding elements from the candidate transposon to create a vector useful for the present invention.

To be introduced into the chromosome, the FRT must be between the outside ends of Tn5 (between 40 and 50 bp, preferably 46 bp of DNA, for each outside end). The transposase will catalyze the movement of any element between these ends. The transposase enzyme is supplied by expressing its gene, also located on the plasmid but not within the outside ends. The plasmid is brought into the cell by standard methods of bacterials transformation (Typically, DNA and prepared cells are simply mixed under conditions where a few of the cells spontaneously take up the plasmid). Once in the cell, the transposase gene is expressed, transposase enzyme is synthesized, and the transposase enzyme then promotes the movement of the DNA segment between the outside ends from the plasmid into the chromosome.

A foreign gene is then introduced on a cloning vector that contains an FRT and a selectable marker. The pEAW127 and 133 constructs (described below) used to put the FRT on the chromosome are designed to make it easy to determine the exact location of the FRT on the chromosome. The cloning vectors used to target the chromosomal FRT are the pEAW116 and pEAW135 constructs (also described below). These cloning vectors contain a replication origin designed to be deleted prior to electroporation for targeting purposes.

For pEAW116 and pEAW135, which bring in exogenous DNA and target it to the chromosomal FRT, one only needs some cells already containing a chromosomal FRT, the vectors (with the desired DNA already inserted into them), and an enzyme to remove the replication origin on the vectors. Two steps in the overall process can be promoted by the FLP recombinase. The segment of the plasmid containing the replication origin is removed. (With pEAW116, this is done with purified FLP recombinase; with pEAW135, it can be done with the restriction enzyme XbaI plus DNA ligase). The abbreviated plasmid DNA is then introduced in the cells by the transformation method described above. Once inside the cell, FLP recombinase is used again to introduce the entire abbreviated plasmid into the chromosome at the site of the FRT. The FLP recombinase used in this latter step is not purified, but instead is expressed from a gene encoding the FLP recombinase present on a separate plasmid (pLH29).

An enzyme capable of removing the replication origin, preferably the FLP recombinase, is provided, preferably in a purified form. Once the cloning vector is introduced into the bacterial cell, an enzyme capable of integrating it into the chromosomal FRT site, preferably the FLP recombinase, is provided, preferably as a plasmid construct. The targeted integrant is then obtained.

The FLP recombinase gene is found on the yeast 2 micron plasmid, a plasmid that is widely distributed in natural strains of the yeast *Saccharomyces cerevisiae*. Cox (1983) describes standard cloning methods.

In a most preferable form of the present invention, the plasmids described below are used to insert the FRT site in the bacterial chromosome, introduce exogenous DNA, and provide FLP recombinase.

The two plasmids in the FLIRT system are likely to be useful in almost all gram-negative bacteria, a class that includes a range of important human pathogens. The only component described below that does not have a wide host range is the plasmid pLH29, used to express the FLP recombinase. If the FLP recombinase were expressed in a broad host range plasmid, such as a vector using the RK2 replicon, the entire system could be used in most, if not all, gram negative bacteria.

EXAMPLES

1. Materials and Methods

Media. X-Gal (5-bromo-4-chloro-3-indolyl-$\beta$-D-galactopyranoside) was from Indofine. IPTG (isopropyl-$\beta$-D-thiogal-actopyranoside) was purchased from Bachem. Antibiotics were purchased from Sigma. Bacterial strains were grown at 37° C. or 30° C. in L broth or on agar plates prepared as described (29) and supplemented with antibiotics as appropriate. Antibiotic concentrations were: ampicillin (Amp), 100 mg/l for cells containing multiple copies of the $\beta$-lactamase gene on plasmids or 20 mg/l for cells containing a single copy of the $\beta$-lactamase gene on the chromosome; kanamycin (Kan), 40 mg/l; tetracycline (Tet), 15 mg/l; chloramphenicol (Cam), 25 mg/l; X-Gal, 40 mg/l. IPTG was used at 0.5 mM or 1 mM as indicated.

Bacterial strains. Key parental strains employed in this work are: CSH26 [F$^-$ ara $\Delta$(lac pro) thi] (29); RZ211 [F$^-$ ara $\Delta$(lac pro) thi srl recA56] (23); and MG1655 (F$^-$, wild-type) (19). The strains RZ211 and MG1655 were obtained from W. Reznikoff (University of Wisconsin) and G. Weinstock (University of Texas-Houston), respectively.

Enzymes and Reagents. Restriction enzymes and bacteriophage T4 DNA ligase were obtained from New England Biolabs, Promega, or Boehringer Mannheim. The FLP recombinase was purified and stored as described elsewhere (46). AMV reverse transcriptase was from Life Sciences. Vent DNA polymerase, Klenow fragment and linkers were purchased from New England Biolabs. Sequencing of DNA in experiments involving the FLIRT system was performed using the Sequenase version 2.0 DNA sequencing kit from Amersham Life Science. Bacterial alkaline phosphatase, BIONICK labeling system, and PHOTOGENE Nucleic Acid detection system were from Gibco BRL. Linkers and biotinylated lambda HindIII digest were from New England Biolabs. All enzymatic reactions were performed essentially as described by Sambrook, et al. (37) or as recommended by the suppliers. Radiolabeled deoxynucleotide triphosphates were obtained from Amersham Life Science. Oligonucleotides were prepared at the DNA synthesis facility in the University of Wisconsin Biotechnology Center or were from Operon Technologies Inc. SeaPlaque agarose was from FMC BioProducts. GENECLEAN was from Bio 101 Inc. Transformation and Bochner selection media were as previously described (9). All chemicals were of analytical grade or better and were purchased from common vendors.

FLIRT System Vectors.

(i) Vectors for the delivery of exogenous DNA. A cloning vector for convenient targeting of exogenous DNA to the bacterial chromosome is pEAW116. To create pEAW116, pJFS36 (42) was digested with BamHI, the ends were filled in, and ClaI linkers were ligated at this site. The resulting construct was digested with ClaI and SphI. A synthetic DNA fragment, with ClaI and SphI ends, containing a short polylinker with HindIII, PstI and SalI sites and an FRT in the same orientation as the FRT already present in pJFS36, was ligated to the prepared vector. The resulting plasmid (now with two SalI sites) was partially digested with SalI and the ends filled in. The tetracycline resistance gene from Tn10 was ligated to the filled-in SalI site, and a construct was chosen in which the Tet$^R$ gene had been inserted in the polylinker between the FRTs. This plasmid was then isolated and digested at HindIII. A short synthetic polylinker containing one HindIII sticky end, sites for KpnI, SmaI, NotI, NheI, BglII, and another end compatible with HindIII but that does not regenerate a HindIII site after ligation (so that HindIII appears at one but not both ends of the fragment added to the vector), was ligated into the cleaved vector. This plasmid is pEAW116. A variant of pEAW116 was constructed by digesting it at the polylinker SmaI and NheI sites and filling in the ends, and then inserting the wild-type rec$\lambda$ gene and its promoter to generate pEAW118.

(ii) Plasmids for introducing FRT sites on the E. coli chromosome. Plasmid pEAW127 contains an FRT, selectable marker, and polylinker between 56 bp Tn5 outside end (OE) sequences, 19 of which are required for Tn5 transposition. The ampicillin resistance gene, origin of replication, lacIq, and Tn5 transposase are located in the region that is not transposed. The FRT was the minimal wild-type FRT derived from pJFS36 (42). The starting point was plasmid pRZ4828 (Reznikoff unpublished work), constructed by inserting a mini-Tn5 element, containing 56 bp of the Tn5 outer ends and BamHI sites flanking the Tn903 kanamycin resistance gene, into the filled-in BamHI site of pRZ4825 (48). The Tn903 Kan$^R$ gene of pRZ4828 was first deleted by digestion with BamHI. This was replaced with a BamHI fragment with bases 1052–2262 of Tn903 containing the kanamycin resistance gene, a short polylinker containing NotI, KpnI, and DraIII sites, and an FRT, ligated to the BamHI digested pRZ4828. This places all of the sequences between the Tn5 outer ends. In order to facilitate the deletion of the replication origin prior to electroporation, EcoRI sites were placed on either side of the plasmid origin (EcoRI linkers were placed at the filled-in NdeI site, and at the DraI site that is not included in the Amp$^R$ gene).

(iii) Plasmids for FLP expression. The plasmid pLH29 provides for expression of FLP recombinase, regulated by plac along with an integral lacI gene. Construction of this plasmid is described elsewhere (20).

Construction of target strains. MG1655 srl::Tn10 $\Delta$rec$\lambda$1398 was transformed with pLH29 and selected for chloramphenicol resistance. Tet$^S$ mutants were then selected using Bochner medium (9). These were designated MG1655 $\Delta$recA Tet$^S$pLH29. The plasmid pEAW127 (10 $\mu$g) was digested with EcoRI to remove the origin of replication. In order to separate any contaminating undigested pEAW127, the digested DNA was incubated at 65° C. for 10 minutes with an equal volume of 1.5% SeaPlaque low-melting point agarose. This was then loaded in the wells of a horizontal 20 cm long, 0.8% agarose gel and allowed to cool 5 minutes before the 1×TAE buffer was added and the gel was run. The low-melting point agarose matrix trapped the circular DNA in the wells (FMC BioProducts, Hank Daum, III personal communication). The large EcoRI fragment without the origin was excised from the gel, and DNA was eluted using Geneclean. The DNA was self-ligated to circularize for 1 hour at room temperature in a volume of 65 $\mu$l. The ligation mix was extracted once with an equal volume of phenol: chloroform: isoamyl alcohol (25:24:1) and ethanol precipitated. The resulting circular DNA was resuspended and digested with BspLU11I for 1 hour at 37° C. in a volume of 100 $\mu$l. This linearizes any contaminating pEAW127 that only cut once with EcoRI, since the BspLU11I site is between the EcoRI sites. The BspLU11I digest was extracted once with phenol: chloroform: isoamyl alcohol (25:24:1) and ethanol precipitated.

The resulting pEAW127Δori DNA was resuspended in 30 μl H$_2$O. The DNA concentration was determined from the OD260 and 0.2, 0.4, and 0.6 μg DNA were electroporated into 40 μl of electrocompetent MG1655 Δrexλ Tet$^S$/pLH29 cells. Electrocompetent cells were grown in 0.5 mM IPTG, 25 mg Cam/l and prepared according to the procedure from Bio-Rad. Electroporations were performed at 25 μf, 2.5 kV, and 200 Ohms in an ice-cold cuvette, with a 0.2 cm gap, by a Bio-Rad Gene Pulser. The cells were plated on 40 mg/l Kan plates and incubated at 37° C. overnight. Twenty-four Kan$^R$ colonies were picked and screened on Amp plates. Kan$^R$ Amp$^S$ colonies indicate that a transposition event occurred to insert the FRT and Kan$^R$ gene onto the chromosome. Small-scale plasmid DNA preparations were done to confirm the presence of pLH29 as the only plasmid in the cells.

Target strains containing FRT sites located at pre-defined sites in the lac operon were generated by homologous recombination. These strains were used to study the effect of transcription on targeting efficiency, with transcription regulated by IPTG. In these experiments, FLP expression was provided by the plasmid pEAW38, in which the FLP gene is subject to temperature induction (21). For better control of the timing of the IPTG-mediated transcription, a lacy strain was preferred in the study. To obtain lacZ: :FRT lacY construct, strains RR1 (lacZ+lacY$^-$) was first transduced to recD::Tn10 by bacteriophage P1 grown on MG1655 recD::Tn10 (from P. Kiley, University of Wisconsin). Then strains RR1recD and MG1655recD were transformed with ScaI-linearized pLH20 and pLH32, respectively, by electroporation using a Bio-rad Gene Pulser and the protocol recommended by the manufacturer. On the plasmids pLH20 and pLH32, the FRT sites were cloned within the lac operon, so the lac-FRT constructs could replace the original lac sequence on the E. coli chromosome by homologous recombination. The construction of these plasmids is described elsewhere (20). In the case of pLH20 transformation, LacZ$^-$ colonies were screened on IPTG-XGal-LB plates; in the case of pLH32 transformation, LacZ+LacY$^-$colonies were screened on lac-MacConkey plates. The colonies with desired phenotypes were picked, and the chromosomal FRT sites were transduced to wild-type RR1 (for pLH20) and MG1655 (pEAW38) (for pLH32). The colonies were selected for Kan$^R$ and screened for the Lac phenotype. The pLH20 FRT site in RR1 was further transduced to wild-type MG1655 (pEAW38). The final strain derived from pLH20 transformants with the FRT site at lacZ is called MG1655lacZ::FRT(pEAW38); and the final strain derived from pLH32 transformants with the FRT site at lacY is called MG1655lacY::FRT(pEAW38). Phenotypically MG1655lacZ::FRT is LacZ–LacY$^-$, and MG1655lacY::FRT is LacZ+LacY$^-$. The lac locations of the FRT sites were confirmed by Southern analysis (data not shown).

Mapping the genomic location of FRT sites in target strains. Genomic DNA from the target strains was isolated as described (51), and 5 μg was digested with either NheI, PvuII, or SphI for 2 hours at 37° C. There are no sites for these enzymes in the FRT-containing DNA transposed to the chromosome. The digested genomic DNA was extracted once with phenol: chloroform: isoamyl alcohol (25:24:1) and ethanol precipitated. The genomic DNA was ligated to pUC119 digested with XbaI, SmaI, or SphI, which generate ends compatible with NheI, PvuII, and SphI respectively. The ligated DNA was transformed into competent DH5a cells [supE44 ΔlacU169 (φ80 lacZΔM15) hsdR17 recA1 endA1 gyrA96 thi–1 relA1], plated on 40 mg/l Kan plates, and incubated at 37° C. overnight. Kan$^R$ colonies should contain inserts of transposed DNA and flanking genomic DNA. Plasmid DNA from the selected colonies was purified and sequenced using a primer consisting of bases 1091–1074 of Tn903. This reads through the FRT and 56 bp Tn5 outer ends and into the flanking genomic DNA. The Fasta program (GCG) was used to compare the genomic DNA sequences with those in Genbank, and identify the precise locations of the FRT-containing sequences in seven target strains. These were designated MG1655 ΔrecA Tet$^S$ 127FRT#1–#7/pLH29.

The insert for #1 maps next to base 67128 of the lambda clone accession #U29579 comprising the E. coli chromosomal region from 61 to 62 minutes. This is between two unidentified ORFs, o191 and f297. #2 transposed next to base 228222 of the lambda clone with accession number U14003, at 92.8 to 00.1 minutes. This is in unidentified ORF f326b. #3 transposed next to base 2165 of the nagC gene which is at 15.5 minutes on the E. coli chromosome. #4 transposed next to base 49628 of the lambda clone with accession number U00039 comprising the E. coli chromosomal region from 76–81.5 minutes. It is in unidentified ORF o383. #5 transposed next to base 11640 of the clone with accession number D90699 at 12.6–12.9 minutes on the chromosome. It is in the unidentified ORF o110. #6 maps next to base 51888 of the lambda clone with accession number U18997 containing the region from 67.4 to 76.0 minutes. It is in the unidentified ORF f408. #7 maps next to base 19887 in accession number U28379, at approximately 68 minutes. It is in the unidentified ORF f168.

Targeting Trials. The plasmids pEAW116 or pEAW118 were first linearized by FspI digestion. Contaminating undigested plasmid DNA was separated by trapping the circular DNA in 1.5% SeaPlaque low-melting point agarose as described above for pEAW127. The linearized DNA (16.8 μg) was then re-circularized by intramolecular FLP-mediated site-specific recombination. The reaction mixture contained 25 mM N-Tris (hydroxymethyl) methyl-3-aminopropanesulfonic acid (TAPS) buffer (pH 8), 1 mM ethylenediamine tetraacetic acid (EDTA), 2.5 mg/ml bovine serum albumin (BSA), 7.5% PEG 8000, 10.8% glycerol, 180 mM NaCl, and 145 nM FLP recombinase in a total reaction volume of 400 μl, and was carried out at 30° C. for 10 minutes. The reaction was stopped by the addition of 50 μl of a solution containing 30% glycerol, 0.03% bromphenol blue, 30 mM EDTA, 4% SDS. The reaction was loaded on a 0.8% agarose gel at 20 μl/lane and run in 1×TAE (27). The circular deletion product of the FLP reaction was eluted from the agarose (Geneclean) in 20 μl H$_2$O. The DNA concentration was determined by absorption at 260 nm. This DNA (0.03–0.1 μ was electroporated into electrocompetent MG1655 ΔrecA Tet$^S$ 127FRT#3 or #4/pLH29 cells as described above for processed pEAW127. Electroporated cells were selected for Tet$^R$, then picked and screened for Tet$^R$ and Amp$^R$. Tet$^R$, Amp$^S$ colonies indicate targeting. To demonstrate the dependence of targeting on the presence of the FLP protein and a chromosomal FRT, the same procedure was used to electroporate electrocompetent cells of MG1655 ΔrecA Tet$^S$ 127FRT#/pLH29 or Mg1655 ΔrecA Tet$^S$/pLH29, and MG1655 ΔrecA Tet$^S$ 127FRT#4 with processed pEAW118.

Reversibility of Targeting. In a typical experiment, single colonies resulting from targeted integration were isolated. Overnight cultures of these isolates were diluted 100-fold in L broth containing 1 mM IPTG to induce excision or no IPTG as a control. The cells were kept at 30° C. Once the culture reached stationary state (about 6 generations), an aliquot of the culture was transferred to fresh media with 1:100 dilution to resume the growth. At the same time, 0.1 ml of the culture was plated on Amp selective media to determine the number of the cells which still kept the phenotype of an integrant. Also, the same volume of the cultures was plated on LB plates to determine the total number of the cells. The ratio of $Amp^R$ surviving integrants vs. total cells were determined. The excision rate (X) was calculated from the equation: $X = 1 - e^{(ln(r)/n)}$, where r=no. of $Amp^R$ colonies/no. of total colonies and n=number of generations.

Testing for the presence of a functional recA gene by exposure to U.V. light. Overnight-cultured cells to be tested were diluted 1/100 in LB media, and grown for ~1.5 hours to mid-log phase. Cultures (10 ml) were then spun down at 2000 g, washed, resuspended in M9 media at OD600=0.054. Aliquots (2 ml) were placed on sterile uncovered 35 mm plates and shaken gently beneath a UV light source (254 nm). The irradiation was conducted under a photographic red light to prevent photo-reactivation. Irradiation was carried out for an appropriate time at fluence rate 0.8 $J/m^2s$ or 1.6 $J/m^2s$. The lamp was calibrated before each experiment using a J-225 Short Wave UV meter. The exposed (or unexposed control) cells were serially diluted and spread on TYE-Cam20 plates. The plates were then wrapped in tinfoil and incubated overnight at 37° C. Colonies were counted the following day. Each data point represents an average from two experiments.

Southern analysis. Genomic DNA (5 µg) was digested with 20 units of PvuII for 2 hours at 37° C. in a final volume of 50 µl. The DNA was ethanol precipitated and resuspended in 10 µl TE. Each digested DNA was loaded on a 1% agarose gel, along with 1 µl of a 100 µg/ml biotinylated HindIII-digested lambda DNA marker. The gel was run at 50 milliamps in 1×TAE, then photographed after staining in ethidium bromide. The DNA was transferred to PhotoGene nylon membranes and Southern analysis was performed using the procedure specified by Gibco BRL. Probes were made by excising the FRT, kanamycin resistance, and flanking genomic DNA from the subclones in pUC119 used for mapping the FRTs on the MG1655 Δrecλ $Tet^S$ chromosome. EcoRI and HindIII were used for the digestion, and the DNA fragments were separated on a 0.8% agarose gel. The DNA to be used as a probe was eluted from the gel using GENECLEAN, and 1 µg DNA was labeled using the Gibco BRL BIONICK labeling system.

2. Results

We previously described a method for chromosomal targeting of exogenous DNA in E. coli (21). The present work was undertaken to determine the effects of parameters such as transcription, chromosomal location, and the host homologous recombination system on integration efficiency, and to refine the system both to facilitate these experiments and to make the system convenient for general use. The system consists of three elements (I) E. coli target strains, each with a single FRT site located on the chromosome; (II) a plasmid permitting the regulated expression of FLP protein; and (III) a delivery vector for exogenous DNA, containing a drug resistance gene marker as well as an FRT site compatible with the FRT site on the chromosome. We first describe the FLIRT system, which is entirely plasmid-based and designed for general use. We then briefly summarize some results obtain ed with a variant of the bacteriophage λ-based system we reported on previously (21), which investigate some of the parameters that might affect targeting (20).

Figure 1B:
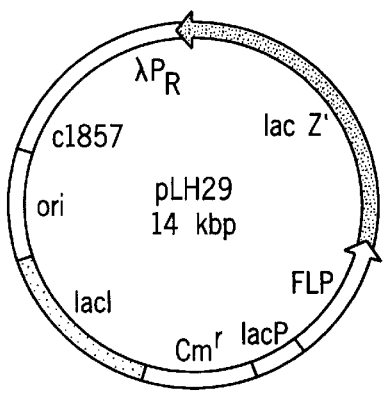
FIG. 1B diagrams FLP expression plasmid pLH29.
Figure 1C:
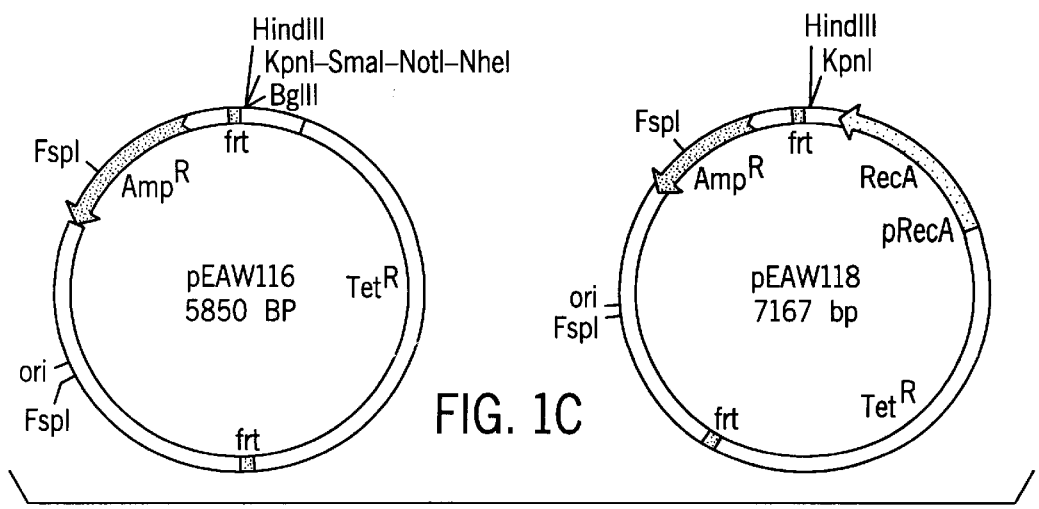
FIG. 1C diagrams plasmids used to introduce exogenous DNA into bacteria and target it to chromosomal FRT sites.

(i) The FLIRT system. The FLIRT system is presented in FIG. 1. FIGS. 1A, B, and C is a diagram of the FLIRT system. A) Plasmids used to introduce FRT sites into the chromosome. Important feature s are described in the text. The plasmid pEAW133 differs from pEAW27 only in the addition of a second FRT site flanking the $Kan^R$ marker. After introduction of the transposed segment to the chromosome and mapping, the additional FRT permits the easy deletion of the $Kan^R$ marker so that Kan selection can be used for other purposes. B) FLP expression plasmid pLH29. Unlike the other components of the system, the plasmid pLH29 contains sequences left over from earlier constructs that are not necessary for (but do not interfere with) its function. C) Plasmids used to introduce exogenous DNA into bacteria and target it to chromosomal FRT sites. The plasmid pEAW116 is designed as a general cloning vector, with a polylinker containing a number of unique restriction sites. The plasmid pEAW135, described in the text, is essentially the same as pEAW116, but lacks XbaI sites other than those within the FRT sites. With pEAW135, the part of the plasmid containing $Tet^R$ and any cloned DNA can be removed and circularized with XbaI plus ligation, eliminating any requirement for purified FLP recombinase. For regulated FLP protein expression, the FLIRT system uses pLH29, which was described in earlier work (20, 21). The improvements in the FLIRT system involve the methods used to introduce FRT sites into the E. coli genome, and to target exogenous DNA to those sites. The system also makes economical use of the most common selectable markers.

(ii) Generating E. coli strains with FRT sites in the genome. The plasmid pEAW127 includes one FRT site and a selectable marker ($Kan^R$) located between the two outside ends (OE) of transposon Tn5 (FRT segment). The Tn5 transposase is encoded elsewhere on the plasmid, and is not transferred to the bacterial chromosome with the FRT site. The site is thus stable and permanent once it is transferred. The replication origin is removed from the plasmid prior to electroporation. Since the plasmid DNA is introduced into the cell only transiently, stable transformation to $Kan^R$ requires the transposition of the FRT segment to the bacterial chromosome or some other replicating DNA element. A second selectable marker that is not part of the FRT segment ($Amp^R$) provides a means to detect suboptimal plasmid preparation or anomalous recombination events.

Figure 2:
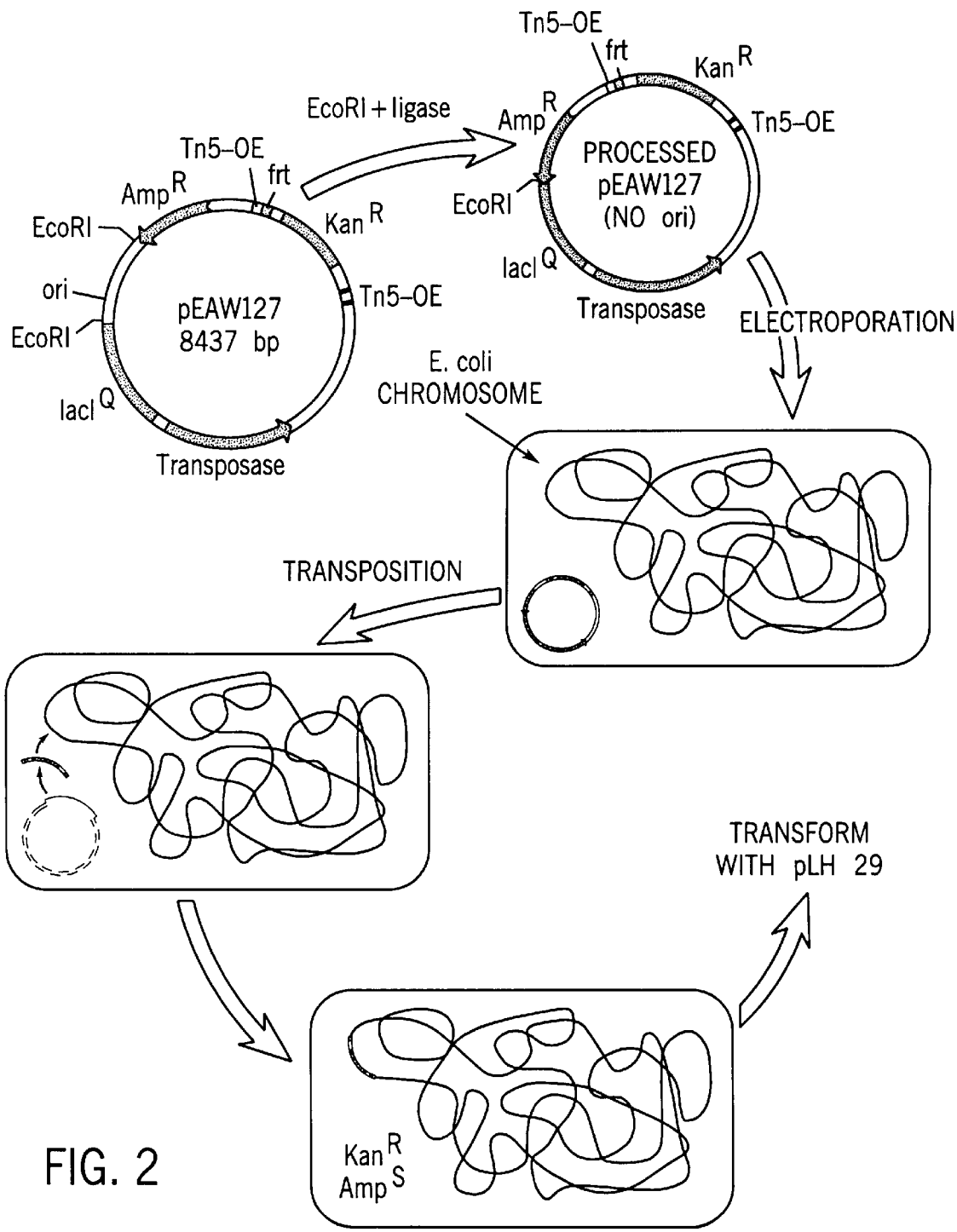
FIG. 2 is a scheme for introducing FRT sites into the bacterial chromosome.

The scheme for generating target strains with pEAW127 is described in FIG. 2, with details presented in Methods. FIG. 2 is a scheme for introducing FRT sites into the bacterial chromosome. The plasmid pEAW127 (or pEAW133) is processed to remove the replication origin. The re-circularized DNA is then electroporated into prepared cells. Without the replication origin, $Kan^R$ is conferred on the cell only if a transposition event occurs transferring the FRT and $Kan^R$-containing segment to the chromosome. The remainder of the electroporated DNA molecule, including the transposase gene and the $Amp^R$ marker, is lost. The transposed segment is structured to facilitate the sequencing of the chromosomal DNA flanking the segment after transposition, allowing the target to be mapped to base pair precision within the E. coli genome database. The plasmid origin is first removed by cleaving with EcoRI and re-ligating. Cleaving again with BspLU11I linearizes any plasmids that retain the origin segment. The circularized plasmids are electroporated into prepared E. coli cells. Transposition of the FRT segment to the chromosome (or a replicating extrachromosomal element) is detected by selection for $Kan^R$. Anomalous recombination events or transformation with intact pEAW127 can be eliminated by screening for Amp$^S$. These generated a total of 6847 Kan$^R$ colonies. Of 214 Kan$^R$ colonies screened (24 each from 9 different electroporations), only 9 (4%), were Amp$^R$. The Amp$^R$ colonies almost invariably arose from pEAW127 DNA from which the ori sequences had not been removed.

The FRT segment that is retained after transposition has short Tn5 ends (56 bp including the 19 bp required to direct transposition). The short length of these repeated end sequences facilitates the sequencing of flanking DNA in order to locate the transposed FRT site with base pair precision. Sequencing primers can be directed at unique sequences in the transposed segment, with sequencing directed outward across the outside ends. A number of the chromosomal segments containing FRT sites were subcloned and sequenced, and the chromosomal positions of the FRT in seven independently chosen target strains are given in FIG. 3.

Figure 3:
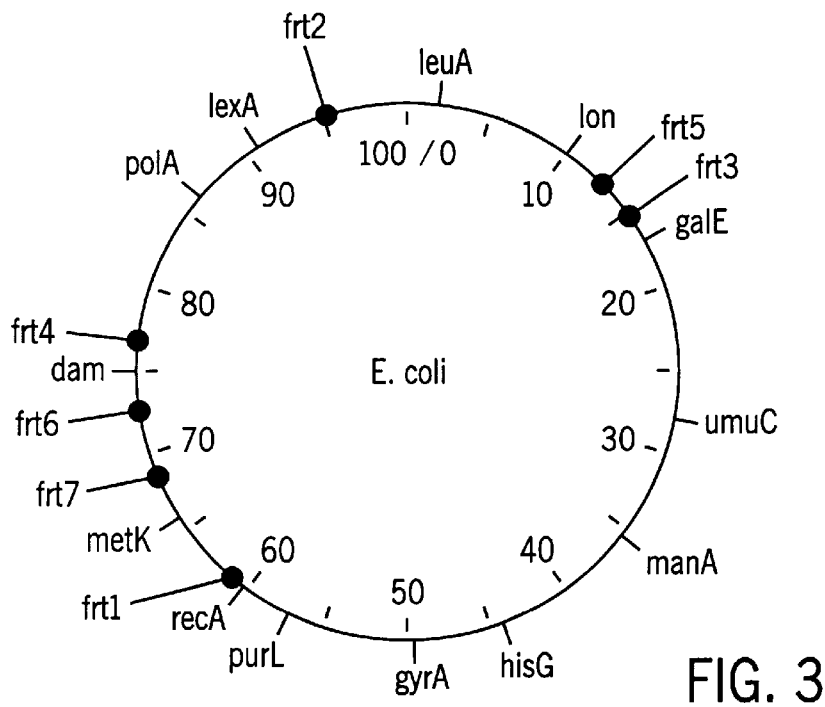
FIG. 3 diagrams the mapped locations of some FRT targets generated by pEAW127.

FIG. 3 diagrams the mapped locations of some FRT targets generated by pEAW127. The base pair locations of these targets are given in Methods. The bacterial strain used was MG1655 ΔrecATet$^S$/pLH29.

A variant of pEAW127 (designated pEAW133, FIG. 1) has been developed which includes a second FRT site on the opposite end of the Kan$^R$ element from the first (FRT2 segment). Once the FRT2 segment is transposed to the chromosome, and the Kan$^R$ element has been used to facilitate selection and sequence-based mapping, the two FRT sites permit the deletion of the Kan$^R$ element while retaining the chromosomal FRT. This simply requires induction of FLP recombinase with IPTG, growth for a few generations without Kan, and screening for a Kan$^S$ colony. This feature should be useful in some applications in that it preserves Kan$^R$ selection for subsequent cloning steps. FLP has previously been used in a similar strategy to remove selectable markers after gene disruption (5).

Figure 4:
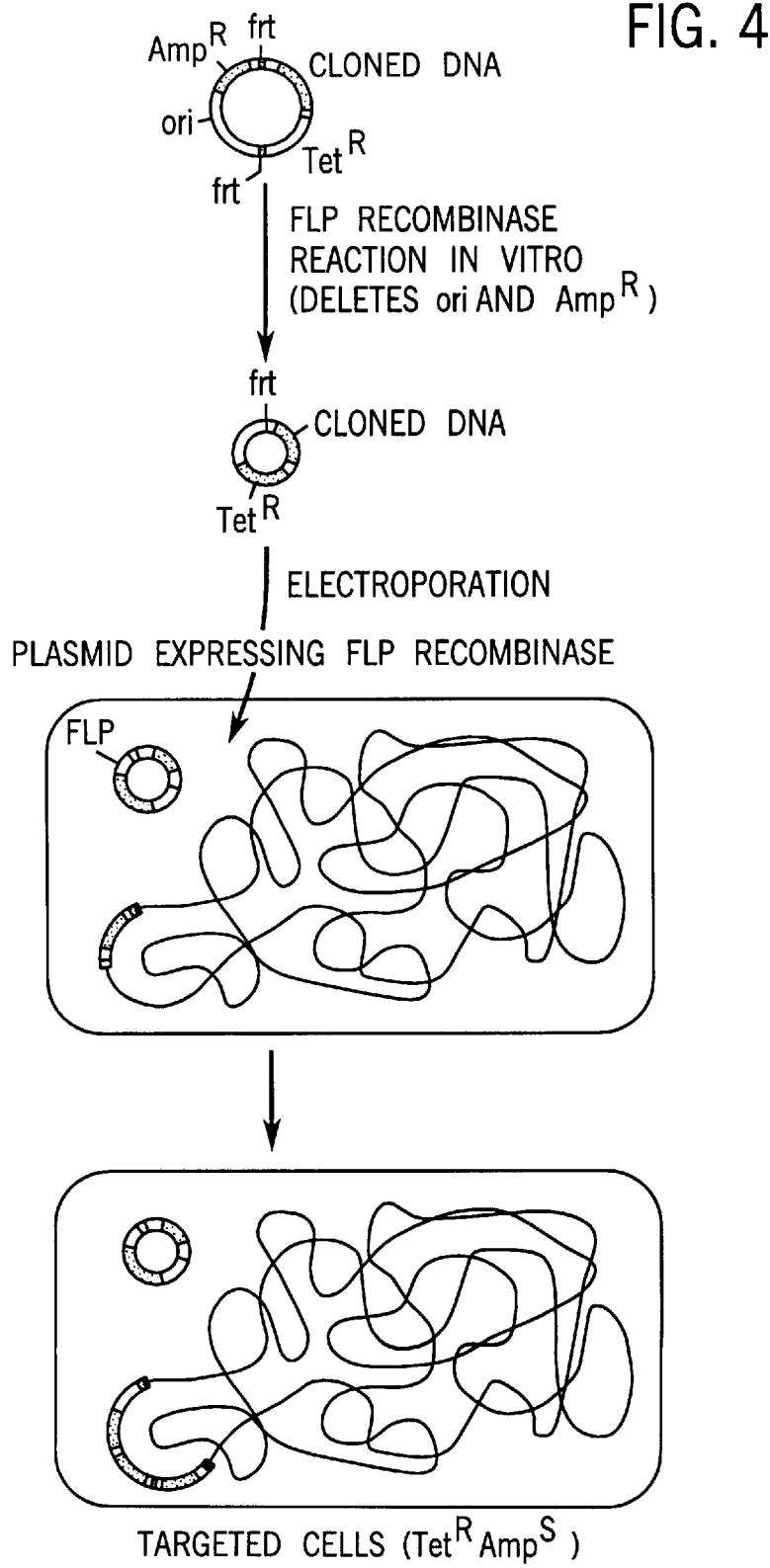
FIG. 4 is a scheme for targeting exogenous DNA to the chromosomal FRTs, using pEAW116 and derivatives.

(iii) Targeting trials. The plasmid pEAW116 features a selectable marker (Tet$^R$) and a polylinker for cloning in a segment flanked by FRT sites. An Amp$^R$ element in the remaining DNA again functions as a marker for anomalous events. Use of this plasmid (FIG. 4) is similar to that outlined above for pEAW127. The plasmid can first be linearized with FspI. FIG. 4 is a scheme for targeting exogenous DNA to the chromosomal FRTs, using pEAW116 and derivatives. The plasmid pEAW116 (or a derivative like pEAW118) is processed to remove the replication origin and Amp$^R$ marker. The re-circularized DNA is then electroporated into prepared cells. Without the replication origin, Tet$^R$ is conferred on the cell only if the electroporated circle is integrated into the chromosomal FRT in an FLP-mediated reaction. A targeted integrant should be Amp$^s$. Events resulting from improperly prepared DNA or anomalous recombination are generally detected as Amp$^R$. This step, not shown in FIG. 4, removes a fragment containing the origin of replication and part of the Amp$^R$ element, and ultimately reduces the background of cells transformed with unprocessed plasmid. Incubation of the larger linear fragment with FLP recombinase in vitro leads to product circles containing only one FRT along with the polylinker and Tet$^R$. These circles are then electroporated into the prepared target cells. Since the circles lack a replication origin, they are not retained unless they are integrated into a replicating DNA molecule, and the potential complexity of introducing a second replication origin into the chromosome is avoided. To illustrate the use of pEAW116, a variant was constructed (pEAW118) in which the recA+ gene and its regulatory elements were cloned into the pEAW116 polylinker.

Virtually all of the Tet$^R$ colonies arose from FLP-mediated targeted integration. In trials with pEAW118, the production of Tet$^R$ colonies was reduced by at least two orders of magnitude if either the chromosomal FRT or the FLP-expressing plasmid was not present (Table 1). Of 265 Tet$^R$ colonies screened over the course of four independent targeting trials, 100% were also Amp$^s$, indicating that the inclusion of unwanted plasmid sequences or transformation by unprocessed pEAW118 did not constitute a significant problem. The cells used in these trials contained a deletion of the recA gene. Interestingly, the targeting trials showed that target #3 (FIG. 3), located in the nagC gene, exhibits a lower than normal targeting efficiency. This may define a relatively "cold spot" for FLP-mediated targeting in the *E. coli* genome. Even here, however, it was not difficult to obtain significant numbers of targeted integrants with pEAW118.

Figures 5A, 5B, 5C:
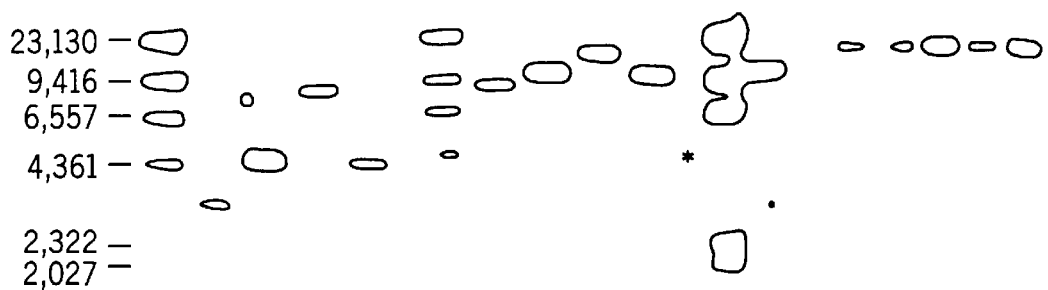
FIGS. 5A and B is a demonstration of FLP-mediated site-specific chromosomal targeting with the FLIRT system and shows Southern analyses of successive steps in targeting.
FIG. 5B is directed to introduction of FRT target #4.
FIG. 5C shows the sensitivity to UV irradiation of the strains analyzed in FIG. 5B, lanes 1–4.
Figure 5D:
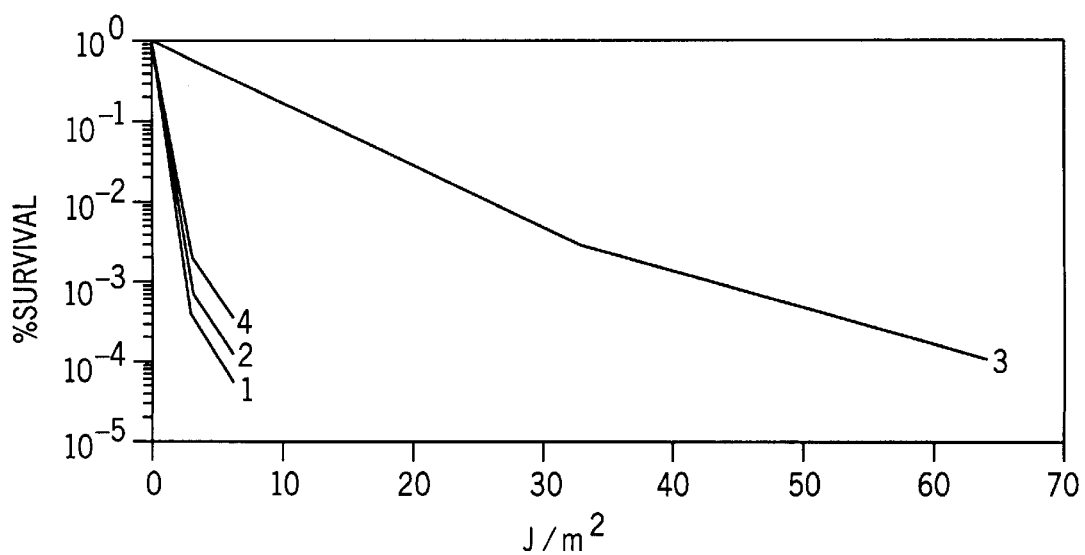

The site-specificity of targeting is illustrated in the Southern blots in FIG. 5. FIGS. 5A and B is a demonstration of FLP-mediated site-specific chromosomal targeting with the FLIRT system. The bacterial strain used was MG1655 ΔrecATet$^S$/pLH29. Panels A and B show Southern analyses of successive steps in targeting. The probe in each case is directed at genome sequences immediately adjacent to the FRT target. Genomic DNA was digested with PvuII in both cases. Referring to FIG. 5, the lanes are: "M," markers generated from a HindIII digest of bacteriophage 1 DNA from New England Biolabs, (DNA fragment sizes are indicated in bp); "1," bacterial strain MG1655 ΔrecATet$^S$/pLH29 without a target FRT; "2," after introduction of FRT target #3 (panel A) or 44 (panel B); "3," after targeting with pEAW118; "4," after FLP-mediated excision of the pEAW118-derived DNA from the chromosome. Panel C shows the sensitivity to UV irradiation of the strains analyzed in panel B, lanes 1–4. Note the elevated resistance observed for the strain from lane 3, reflecting the introduction of a wild-type recλ gene. A probe was directed at genomic sequences adjacent to the chromosomal FRT. Upon introduction of the chromosomal FRT by transposition, the labeled fragment is seen to increase in size by an increment consistent with the introduction of the 1430 bp element derived from pEAW127 (including the FRT plus Kan$^R$; lane 2 in panels A and B). The use of pEAW118 as the source of exogenous DNA adds another 4270 bp when the chromosomal FRT is targeted (lane 3 in panels A and B). Targeting is efficient and reliably site-specific. Six colonies in which processed pEAW118 was integrated into target #4 were selected at random, and examined by Southern analysis. The targeting occurred at the same location in each case (FIG. 5C). The targeted integration was also reversible (lane 4 in panels A and B). As shown in FIG. 5D, the introduction of the DNA from pEAW118 introduces a degree of resistance to UV irradiation that is consistent with the introduction of the recA phenotype into the cell. This phenotype is lost when the targeted DNA is excised.

A potential problem with the use of pEAW116 is the need for processing with the FLP recombinase, which is not yet commercially available[1]. We have constructed a variant of pEAW116 in which all XbaI restriction sites, other than those present in the FRT sites, have been removed. The plasmid is pEAW135 (not shown, essentially identical to pEAW116), and it allows the removal of the replication origin by cleavage with XbaI followed by circularization (by ligation) of the fragment containing the Tet$^S$ element plus any cloned DNA. If the cloned DNA does not contain an XbaI site, this alternative eliminates the need for FLP recombinase.

Figure 6:
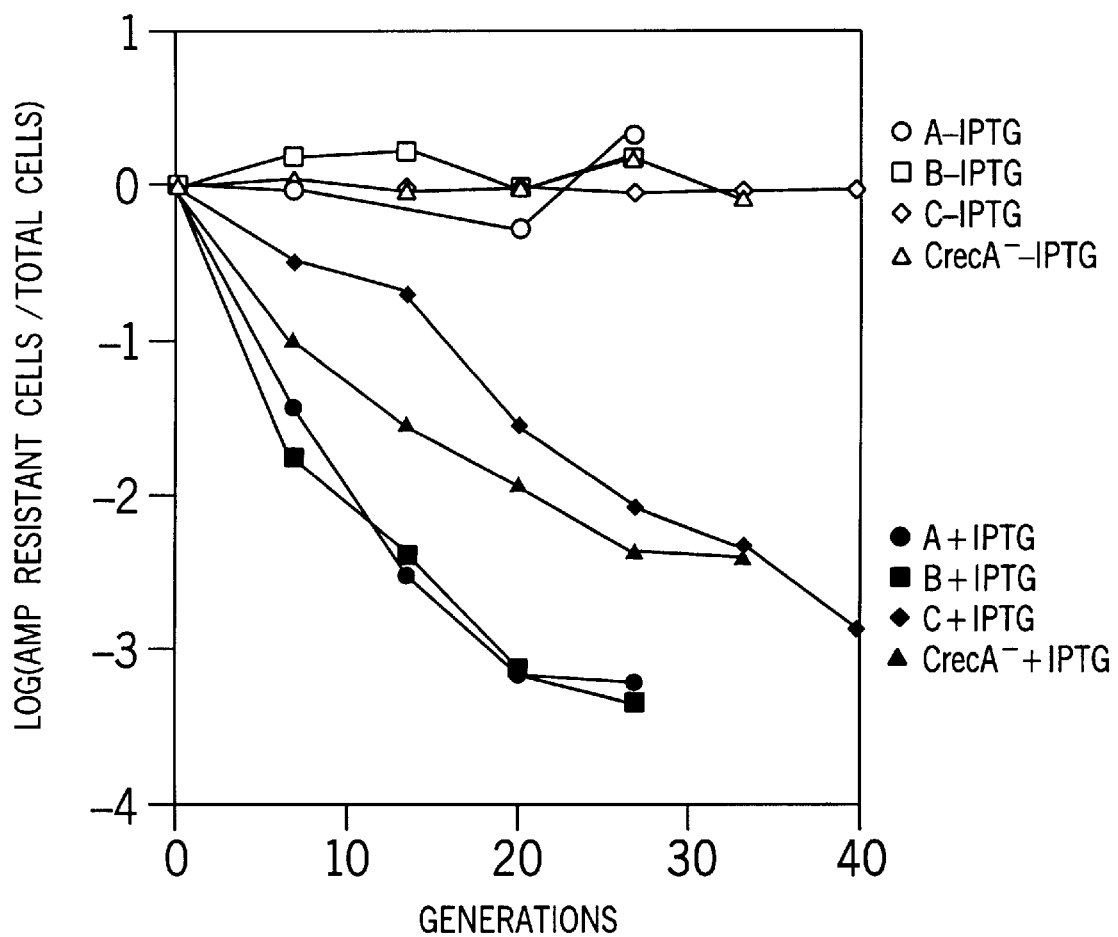
FIG. 6 graphs rates of FLP-mediated excision of targeted DNA from a chromosomal FRT site.

(iv) Integrant stability. To study the reversibility of the site-specific integration event in more detail, integrants obtained with a precursor of the FLIRT system (20, 21) were examined to determine the rate of integrant excision. Colonies resulting from a λFRT36 (21) X chromosomal FRT integration reaction were isolated, and grown in L broth with 1 mM IPTG. The FLP recombinase was expressed using pLH29, which is also used in the FLIRT system. At intervals, cells recovered were plated on both LB plates and selective media. A typical result is shown in FIG. 6. We also ran controls where no IPTG was added. The ratio of surviving integrants/total cells decreased sharply in the first 6 generations of growth in IPTG-containing media. Later, the decrease seemed to slow down. The estimated excision rate during the first six generations was about 30% per generation on average, with a range of 25% to 40% per generation for 6 independent excision experiments. There was no detectable excision when the integrants were grown in media without IPTG (FIG. 6). FIG. 6 graphs rates of FLP-mediated excision of targeted DNA from a chromosomal FRT site. Experiments were carried out as described in Methods. The presence or absence of IPTG is indicated. The targets A, B, C, and CrecA– each have a single chromosomal FRT in CSH26, with the last of these transduced to recA56. The FRT sites were introduced on bacteriophage l/Tn5 vectors using strategies described elsewhere (20, 21). Targets A, B, and C correspond to targets 3601, 3602, and 3621, respectively, described previously (20, 21). FLP expression was provided by pLH29. All of the strains were originally targeted with λFRT36 (21), and it is the precise excision of this DNA element that is monitored in this experiment.

To determine if integrants that survived after 25 generations were resistant to excision, the cells that remained $Amp^R$ were isolated and grown in fresh media with 1 mM IPTG. The integrated DNA in these cells can be excised as efficiently as the original integrants, again with an excision rate about 30% per generation. We found no evidence for a subclass of cells in which excision was reduced or did not occur. In addition, cells in which the integrated DNA had been excised could be subjected to targeting trials again, and the apparent integration frequency of these cells was about the same as the apparent integration frequency of the parental target strains (data not shown). This result shows that the targeting system based on FLP site-specific recombination reactions is fully reversible and indicates that the FRT sites in the chromosome remain intact during repeated integration and excision. We also compared the excision rate of RecA+ and RecA⁻ integrants. The rate was about the same in two independent trials, whether they had RecA+ or RecA⁻ phenotypes (FIG. 6).

Rates of excision were very similar in trials carried out with integrants generated with the FLIRT system, using the protocol described in Methods. However, we have recently found that most of the excision occurs in the stationary phase of cell growth rather than the exponential phase. If cultures are regularly diluted to maintain exponential growth, little excision is observed even in the presence of IPTG. The simplest way to generate cells with the integrated DNA excised, therefore, is to grow them up in an overnight culture and then select for excision immediately. In the absence of IPTG, little excision is observed even in stationary phase cells.

(v) Effects of transcription from a nearby promoter. It is known that transcription affects the topology of the DNA template, generating positive supercoils ahead of the RNA polymerase and negative supercoils behind (49). In addition, RNA polymerase might at least transiently block a chromosomal FRT site in its path during transcription. To determine how transcription might affect the efficiency of site-specific targeting into the E. coli chromosome, we introduced our chromosomal FRT constructs at a fixed position on the chromosome within the lac operon. We made two constructs. In the strain designated as MG1655lacZ-FRT, the FRT site is located within the lacZ gene, about 80 nucleotides downstream of the transcription initiation site. In the second construct, designated as MG1655 lacY-FRT, the FRT site is located within the lacY gene. In this construct, the lacZ gene remains intact, and the transcription from the lac promoter can be assessed by the expression of the lacZ gene product. The positions of FRT sites in these strains were confirmed by Southern analysis. To mediate targeting, both of the strains contain the FLP expression plasmid pEAW38 (21). The expression of the FLP recombinase on this plasmid is heat inducible. This allowed us to independently induce the lac-FRT operon by adding IPTG to the medium and FLP gene transcription by shifting the culture to high temperature as needed.

Our results showed that transcription from the lac promoter did not have a dramatic effect on targeting frequency (Table 2). The apparent integration frequency of MG1655lacZ-FRT slightly increased when 1 mM IPTG was added. When the FRT site was moved farther downstream to the lacY region, there was no detectable difference in integration frequency with or without IPTG. These experiments have been repeated at least 8 times for the lacZ-FRT construct and 3 times for lacY-FRT construct. A modest effect of transcription (2–3 fold) was always observed for lacZ-FRT. We conclude that the FLP mediated integration is only moderately sensitive to transcription at the lac locus.

Figure 7:
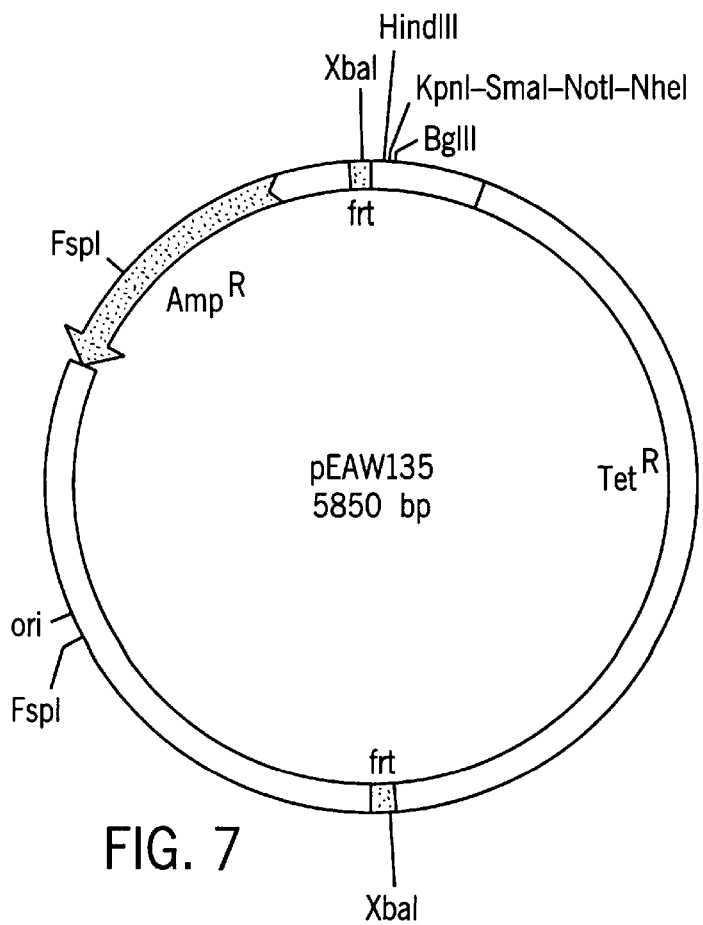
FIG. 7 is a diagram of pEAW135.

We have recently implemented new system refinements. We use a variant of pEAW116 called pEAW135, in which all XbaI restriction sites (except those in the FRT sites) have been removed. FIG. 7 diagrams pEAW135. This allows a user to remove the replication origin with XbaI enzyme. pEAW116 involves the use of purified FLP recombinase and it would be an advantage to use the widely available XbaI.

The construct shown in FIG. 7 does not eliminate the reliance of the system on the FLP recombinase. There are several steps needed to get DNA cloned into pEAW116 or its derivatives into the bacterial chromosome (referring to FIG. 4). In the first step, the plasmid must be processed in vitro by FLP recombinase to eliminate the left half of the plasmid sequences depicted in FIG. 1C (between the FRT sites at the top and bottom of the circle). The FLP recombinase reacts between the FRT sites as indicated at the top of FIG. 4, creating a smaller circle containing the sequences in the right half of the plasmid shown in FIG. 1C. This eliminates in particular the sequence called "ori", which would be deleterious to the cell if introduced into the chromosome. The plasmid shown in FIG. 7 allows one to instead cut the plasmid at the two FRT sites (which both have a recognition site for XbaI), and then use DNA ligase to make the same circle (including the right half of the sequences shown in FIG. 1C) that FLP recombinase is required for in pEAW116. This substitution of XbaI works only if there is no XbaI site in the DNA a researcher may clone into the plasmid. In addition, once the processed DNA circles are introduced into the cell, introduction of the circle into the chromosome still depends on the presence of FLP recombinase inside the cell (provided by expression from a plasmid such as pLH29) in order to get the circle into the chromosome. (This step shown about half-way down in FIG. 4.) This is true for both pEAW116 and for the new FIG. 7 construct, pEAW135. The new construct simply gets around the use of FLP recombinase in the test tube in at least some cases. In effect, there are two steps requiring FLP recombinase, one outside the cell (in vitro) and one inside the cell (in vivo). The new construct affects only the former (which is the only one requiring FLP recombinase in a purified form).

3. Discussion

FLIRT is a plasmid-based system for FLP-mediated chromosomal targeting and genome rearrangement in E. coli. FRT sites can be introduced into the chromosome of almost any E. coli strain, and mapped to base pair precision. The chromosomal FRT sites are stable once introduced, since the Tn5 transposase gene is not included in the DNA transposed to the chromosome. The FRT can, in principle, be introduced at any chromosomal location where Tn5 can transpose. Once on the chromosome, the FRT becomes an integration site for exogenous DNA. The procedure for bringing in exogenous DNA makes use of a plasmid cloning vector, processed prior to electroporation to remove the replication origin. Chromosomal integration is efficient and reliably site-specific. The targeted integrants are stable as long as FLP recombinase is not induced. However, integration is reversible in the presence of FLP recombinase. Transcription initiation at an upstream promoter (Lac) had only a modest effect on targeted integration frequencies, although we cannot rule out the possibility that other promoters might affect targeting to a greater extent.

A number of parameters that might affect targeting have been explored previously, in some cases with FLP-based systems that are precursors of FLIRT (20, 21). All of the recombination reactions are recA independent, and the FLP-mediated processes were several orders of magnitude more efficient and reliable than events mediated by homologous genetic recombination (20). There is no detectable pseudo-FRT site in the E. coli genome that could react with a normal FRT site, helping to ensure that the background of anomalous recombination events is low. A survey of 88 independently selected strains with chromosomal FRTs, placed on the chromosome as randomly as can be done with Tn5 transposition, indicates that FLP-mediated chromosomal targeting is largely independent of the chromosomal location of the FRT site (20). However, we have detected at least two apparent "cold spots" in the genome that always give 10 to 100-fold lower targeting frequencies than the others. First, 4 of the 88 surveyed sites, all located within a 10,000 bp region encompassing the cyo operon (20) gave lower than normal targeting frequencies. The other 84 surveyed target sites were not mapped. Of the 7 precisely mapped chromosomal FRTs used in the current study (FIG. 3), one located in the nagC gene (#3) also gave lower than normal targeting frequencies. We do not know why these few chromosomal FRTs were less efficient in targeting trials than normal, but targeting efficiency even with these was high enough that targeted integrants were easily obtained.

A few features of the FLIRT system or applications of site-specific recombination have been previously developed in other bacterial systems. First, a method for deleting a plasmid ColE1 origin in vivo by placing it between two phage f1 replication origins has been described (45). The result is a kind of suicide vector that can be used for chromosomal allele replacements. In the FLIRT system, provision has been made to remove plasmid replication origins enzymatically in vitro where necessary. The Cre-loxP system has been used to generate precise chromosomal deletions. Homologous recombination was used to position loxP sites on either side of the DNA to be deleted, followed by induction of the Cre recombinase on a suitable expression plasmid (1). Controlled deletion can be used to study gene function, and a similar approach has been used in eukaryotic organisms in a range of studies enumerated in the Introduction. The FLIRT system could expand the range of experiments that could be accomplished with such a precise deletion construct. If FRT sites were similarly positioned on either side of a chromosomal bacterial gene or regulatory site [perhaps using the allele replacement strategy of Slater and Maurer (45)], the FLIRT plasmid pLH29 could be adapted to delete the DNA and pEAW116 or derivatives could be used to target variants of the same or different DNA segments to the single FRT that would be left behind at the same chromosomal location. Precise deletion with FLP has also been coupled to a conditional replication origin to permit the excision and amplification of large chromosomal segments in vivo, permitting their isolation as large plasmids (33). The FLIRT system generally complements these applications.

Site-specific recombination may be usefully applied when the exogenous DNA has no homology to the bacterial genome, more precise control or higher efficiency is required in the integration reaction to facilitate the independent introduction of several alleles of a gene into an isogenic background, the exogenous DNA is required only transiently to facilitate one step in strain construction, or a recA background is required for genetic complementation tests. Allelic or other genetic comparisons can be made without the complication of chromosomal position effects. FLIRT simplifies the task of placing any DNA sequence directly onto the chromosome. Parts or all of the system should be adaptable for use in other bacterial species.

The technique should also facilitate the study of broader genome structure. Sequences that readily take up altered DNA structures can be positioned at a variety of locations in the chromosome and their effects on DNA or cellular metabolism studied. New replication origins, promoters, or termination sites for replication or transcription could be introduced. Although the use of Tn5 introduces the FRT sites into more or less random locations in the chromosome, the FRTs can be placed more precisely if a selection exists for the disruption of a particular gene. Note that the use of pEAW133 to introduce FRTs into the chromosome allows for the simple removal of the $Kan^R$ selection marker once the FRT site is mapped. This would set the stage for introducing a second FRT site somewhere else in the same genome. Expression of FLP recombinase would then lead to the inversion or deletion of the intervening genomic DNA. There are obviously many other possibilities.

4. Prophetic Applications of the FLIRT System

The FLIRT system makes use of natural transposition and site-specific recombination systems to permit the reversible introduction of cloned DNA into defined sites on a bacterial chromosome. FLIRT will be very useful in basic and applied research involving bacteria. A series of likely applications is summarized above.

Beyond these basic applications, we can imagine a variety of additional uses in the future. A major effort is now underway to engineer bacteria so that they possess new metabolic pathways useful to industry. One possibility is to create bacteria capable of efficiently degrading toxins in chemical waste dumps or sewage treatment facilities. Introducing new metabolic processes to a bacteria would require the introduction of the genes (DNA) encoding the enzymes required for the process. The introduction of new genes to a bacterial chromosome for this purpose could be greatly simplified with FLIRT.

The FLIRT system is flexible and can be expanded to allow for quite complicated genetic constructs. The FRT site used by the FLP recombinase (at the heart of FLIRT) can be modified to produce multiple FRTs. A minimal FRT site consists of two inverted 13 bp repeats, separated by an 8 bp spacer. The FLP recombinase binds to the repeat sequences. The FRT can be modified within the spacer region. The altered FRT sites would be functional, but an FRT with a particular spacer sequence will react only with another FRT with exactly the same sequence. This property (described in Umlauf and Cox (1988) *EMBO Journal* 7:1945–1852) could allow the introduction of several distinct FRT sites onto a bacterial chromosome. We could, for example, modify the FRT sites on the plasmid pEAW133. Once on the chromosome, each of these FRT sites could then be independently targeted with cloned DNA. Hence, if one introduces different modified FRTs at different places in the bacterial chromosome, one could target each independently by altering the FRT on the plasmid pEAW116 to be identical to the particular chromosomal FRT that one wished to target. This would allow the introduction of several distinct cloned DNA segments at distinct and definable locations about the chromosome.

Another application of FLIRT, or FLIRT components, would be in the area of new antibiotics to treat bacterial infections. The recombination systems in FLIRT could be engineered into a delivery system to bring DNA encoding proteins toxic to the bacteria into their genomes. Such an application might use genetically-engineered bacteriophages, which could provide the mechanism needed to get the DNA into the bacteria efficiently. The DNA itself would encode the toxic proteins and would also include the elements of FLIRT needed to integrate the DNA into the bacterial genome. When the bacteria expressed the new DNA, it would, in effect, kill itself.

REFERENCES

1. Ayres, E. K., V. J. Thomson, G. Merino, D. Balderes, and D. H. Figurski. 1993. Precise deletions in large bacterial genomes by vector-mediated excision (VEX). The trfA gene of promiscuous plasmid RK2 is essential for replication in several gram-negative hosts. *J. Mol. Biol.* 230:174–85.
2. Baubonis, W. and B. Sauer. 1993. Genomic targeting with purified Cre recombinase. *Nuc. Acids Res.* 21:2025–9.
3. Bayley, C. C., M. Morgan, E. C. Dale, and D. W. Ow. 1992. Exchange of gene activity in transgenic plants catalyzed by the Cre-lox site-specific recombination system. *Plant Mol. Biol.* 18:353–61.
4. Bernet, A., S. Sabatier, D. J. Picketts, R. Ouazana, F. Morle, D. R. Higgs, and J. Godet. 1995. Targeted inactivation of the major positive regulatory element (HS-40) of the human alpha-globin gene locus. *Blood* 86:1202–11.
5. Cherepanov, P. P. and W. Wackernagel. 1995. Gene disruption in *Escherichia coli*: TcR and KmR cassettes with the option of Flp-catalyzed excision of the antibiotic-resistance determinant. *Gene* 158:9–14.
6. Cox, M. M. 1983. The FLP protein of the yeast 2-microns plasmid: expression of a eukaryotic genetic recombination system in *Escherichia coli*. *Proc. Natl. Acad. Sci. USA* 80:4223–7.
7. Cox, M. M. 1989. DNA Inversion in the 2 mm Plasmid of *Saccharomyces cerevisiae*. p. 661–670 in Berg, D. E. and M. M. Howe (Ed.), Mobile DNA. American Society for Microbiology, 8. Craig, N. L. 1988. The mechanism of conservative site-specific recombination. *Ann. Rev. Genet.* 22:77–105.
9. Davis, R. W., D. Botstein, and J. R. Roth. 1980. Advanced Bacterial Genetics. Cold Spring Harbor, N.Y.: Cold Spring Harbor Laboratory.
10. DiSanto, J. P., W. Muller, G. D. Guy, A. Fischer, and K. Rajewsky. 1995. Lymphoid development in mice with a targeted deletion of the interleukin 2 receptor gamma chain. *Proc. Natl. Acad. Sci. USA* 92:377–81.
11. Fiering, S., E. Epner, K. Robinson, Y. Zhuang, A. Telling, M. Hu, D. I. Martin, T. Enver, T. J. Ley, and M. Groudine. 1995. Targeted deletion of 5'HS2 of the murine beta-globin LCR reveals that it is not essential for proper regulation of the beta-globin locus. *Genes & Develop.* 9:2203–13.
12. Fiering, S., C. G. Kim, E. M. Epner, and M. Groudine. 1993. An "in-out" strategy using gene targeting and FLP recombinase for the functional dissection of complex DNA regulatory elements: analysis of the beta-globin locus control region. *Proc. Natl. Acad. Sci. USA* 90:8469–73.
13. Fukushige, S. and B. Sauer. 1992. Genomic targeting with a positive-selection lox integration vector allows highly reproducible gene expression in mammalian cells. *Proc. Natl. Sci. USA* 89:7905–9.
14. Fuse, T., H. Kodama, N. Hayashida, K. Shinozaki, M. Nishimura, and K. Iba. 1995. A novel Ti-plasmid-convertible lambda phage vector system suitable for gene isolation by genetic complementation of *Arabidopsis thaliana* mutants. *Plant J.* 7:849–56.
15. Gage, P. J., B. Sauer, M. Levine, and J. C. Glorioso. 1992. A cell-free recombination system for site-specific integration of multigenic shuttle plasmids into the herpes simplex virus type 1 genome. *J. Virol.* 66:5509–15.
16. Golic, K. G. 1994. Local transposition of P elements in Drosophila melanogaster and recombination between duplicated elements using a site-specific recombinase. *Genetics* 137:551–63.
17. Golic, K. G. and S. Lindquist. 1989. The FLP recombinase of yeast catalyzes site-specific recombination in the Drosophila genome. *Cell* 59:499–509.
18. Gu, H., Y. R. Zou, and K. Rajewsky. 1993. Independent control of immunoglobulin switch recombination at individual switch regions evidenced through Cre-loxP-mediated gene targeting. *Cell* 73:1155–64.
19. Guyer, M. S., R. R. Reed, J. A. Steitz, and K. B. Low. 1981. Identification of a sex factor affinity site in *E. coli* as gsd. *Cold Spring Harbor Symp. Quant. Biol.* 45:135–140.
20. Huang, L. C. 1992. A bacterial model system for chromosomal targeting. University of Wisconsin-Madison: Ph.D. thesis.
21. Huang, L. C., E. A. Wood, and M. M. Cox. 1991. A bacterial model system for chromosomal targeting. *Nuc. Acids Res.* 19:443–8.
22. Huang, L. C. E. A. Wood, and M. M. Cox. 1997. Convenient and reversible targeting of exogenous DNA into a bacterial chromosome by use of the FLP recombinase: the FLIRT system. *J. Bacter.* 179:6076–6083.
23. Jayaram, M. 1994. Phosphoryl transfer in Flp recombination: a template for strand transfer mechanisms. *Trends Biochem. Sci.* 19:78–82.
24. Johnson, R. C., J. C. Yin, and W. S. Reznikoff. 1982. Control of Tn5 transposition in *Escherichia coli* is mediated by protein from the right repeat. *Cell* 30:873–82.
25. Lakso, M., B. Sauer, B. J. Mosinger, E. J. Lee, R. W. Manning, S. H. Yu, K. L. Mulder, and H. Westphal. 1992. Targeted oncogene activation by site-specific recombination in transgenic mice. *Proc. Natl. Acad. Sci. USA* 89:6232–6.
26. Lasko, M., J. G. Pichel, J. R. Gorman, B. Sauer, Y. Okamoto, E. Lee, F. W. Alt, and H. Westphal. 1996. Efficient in vivo manipulation of mouse genomic sequences at the zygote stage. *Proc. Natl. Acad. Sci. USA* 93:5860–5.

27. Leslie, N. R. and D. J. Sherratt. 1995. Site-specific recombination in the replication terminus region of *Escherichia coli*: functional replacement of dif. *Embo J.* 14:1561–70.
28. Maniatis, T., E. F. Fritsch, and J. Sambrook. 1982. Molecular Cloning: A Laboratory Manual. Cold Spring Harbor, N.Y.: Cold Spring Harbor Laboratory.
29. Medberry, S. L., E. Dale, M. Qin, and D. W. Ow. 1995. Intra-chromosomal rearrangements generated by Cre-lox site-specific recombination. *Nuc. Acids Res.* 23:485–90.
30. Miller, J. H. 1972. Experiments in Molecular Genetics. Cold Spring Harbor, New York: Cold Spring Harbor Laboratory.
31. Morris, A. C., T. L. Schaub, and A. A. James. 1991. FLP-mediated recombination in the vector mosquito, *Aedes aegypti*. *Nuc. Acids Res.* 19:5895–900.
32. O'Gorman, S., D. T. Fox, and G. M. Wahl. 1991. Recombinase-mediated gene activation and site-specific integration in mammalian cells. *Science* 251:1351–5.
33. Osborne, B. I., U. Wirtz, and B. Baker. 1995. A system for insertional mutagenesis and chromosomal rearrangement using the Ds transposon and Cre-lox. *Plant J.* 7:687–701.
34. Posfai, G., M. Koob, Z. Hradecna, N. Hasan, M. Filutowicz, and W. Szybalski. 1994. In vivo excision and amplification of large segments of the *Escherichia coli* genome. *Nuc. Acids Res.* 22:2392–8.
35. Qin, M., E. Lee, T. Zankel, and D. W. Ow. 1995. Site-specific cleavage of chromosomes in vitro through Cre-lox recombination. *Nuc. Acids Res.* 23:1923–7.
36. Ramirez, S. R., P. Liu, and A. Bradley. 1995. Chromosome engineering in mice. *Nature* 378:720–4.
37. Reznikoff, W. S. 1993. Ann. Rev. Microb. 47:945–963.
38. Sadowski, P. D. 1995. The Flp recombinase of the 2-microns plasmid of Saccharomyces cerevisiae. *Prog. Nuc. Acid Res. Mol. Biol.* 51:53–91.
39. Sambrook, J., E. F. Fritsch, and T. Maniatis. 1989. Molecular Cloning: A Laboratory Manual. 2nd ed. Cold Spring Harbor, N.Y.: Cold Spring Harbor Laboratory.
40. Sauer, B. 1992. Identification of cryptic lox sites in the yeast genome by selection for Cre-mediated chromosome translocations that confer multiple drug resistance. *J. Mol. Biol.* 223:911–28.
41. Sauer, B. 1993. Manipulation of transgenes by site-specific recombination: use of Cre recombinase. *Methods Enzym.* 225:890–900.
42. Sauer, B. 1994. Recycling selectable markers in yeast. *Biotechniques* 16:1086–8.
43. Sauer, B. 1994. Site-specific recombination: developments and applications. *Curr. Opin. Biotech.* 5:521–7.
44. Senecoff, J. F., R. C. Bruckner, and M. M. Cox. 1985. The FLP recombinase of the yeast 2-micron plasmid: characterization of its recombination site. *Proc. Natl. Acad. Sci. USA* 82:7270–4.
45. Slater, S. and R. Maurer. 1993. Simple phagemid-based system for generating allele replacements in *Escherichia coli*. *J. Bacteriol.* 175:4260–2.
46. Smith, A. J., S. M. De, A. B. Kwabi, P. A. Heppell, H. Impey, and P. Rabbitts. 1995. A site-directed chromosomal translocation induced in embryonic stem cells by Cre-loxP recombination. *Nature Genet.* 9:376–85.
47. Van, D. J., M. Fornerod, R. B. Van, and G. Grosveld. 1995. Cre-mediated site-specific translocation between nonhomologous mouse chromosomes. *Proc. Natl. Acad. Sci. USA* 92:7376–80.
48. Waite, L. L. and M. M. Cox. 1995. A protein dissociation step limits turnover in FLP recombinase-mediated site-specific recombination. *J. Biol. Chem.* 270:23409–23414.
49. Wang, P., M. Anton, F. L. Graham, and S. Bacchetti. 1995. High frequency recombination between loxP sites in human chromosomes mediated by an adenovirus vector expressing Cre recombinase. *Somatic Cell & Molec. Genet.* 21:429–41.
50. Weinreich, M. D., H. Yigit, and W. S. Reznikoff. 1994. Overexpression of the Tn5 Transposase in *Escherichia coli* results in filamentation, aberrant nucleoid segregation, and cell death: analysis of *E. coli* and transposase suppressor mutations. *J. Bacteriol.* 176:5494–5504.
51. Wu, H. Y., S. H. Shyy, J. C. Wang, and L. F. Liu. 1988. Transcription generates positively and negatively supercoiled domains in the template. *Cell* 53:433–40.
52. Xu, T. and G. M. Rubin. 1993. Analysis of genetic mosaics in developing and adult Drosophila tissues. *Development* 117:1223–37.
53. Yu, G. L. and E. H. Blackburn. 1990. Amplification of tandemly repeated origin control sequences confers a replication advantage on rDNA replicons in tetrahymena thermophila. *Molec. Cell. Biol.* 10:2070–2080.

TABLE 1

The FLIRT system: Targeting efficiency with pEAW118.[a]

| | FLIRT System | | |
|---|---|---|---|
| Experiment | Complete | No chromosomal FRT | No FLP recombinase |
| 1 | 97 | 0 | 1[b] |
| 2 | 63 | 0 | 1[c] |
| 3 | 23 | 0 | 0 |
| 4 | 82 | 0 | 0 |

[a]The bacterial strain used was MG1655 ΔrecATet[s]/pLH29, with FRT target #4 (FIG. 3). The four electroporation experiments were all done on different days. Each used 0.03 mg of pEAW118 DNA, processed to remove the replication origin and Amp[R] marker as described in Methods. For each experiment, separate side-by-side electroporation trials were done with bacterial strains identical to MG1655 ΔrecATet[s]/pLH29 except that they lacked either the chromosomal FRT target or pLH29 (which expresses FLP recombinase). Numbers reflect the total number of Tet[R] colonies obtained in a trial.
[b]Colony was Amp[r].
[c]Colony was Amp[s].

TABLE 2

The effect of transcription initiation from an upstream promoter on targeting efficiency.[a]

| | no. of colonies per plate[b] | | Ratio of +IPTB/- |
|---|---|---|---|
| Strain | +IPTG | −IPTG | IPTG (mean ± SD)[c] |
| Non-target | 1 | 0 | |
| MG1655lacZ-FRT | 139 | 39 | 242 ± 0.71 (n = 8) |
| MG1655lacY-FRT | 206 | 247 | 1.11 ± 0.25 (n = 3) |

[a]Introduction of exogenous DNA was accomplished by phage infection rather than by electroporation. Results of a typical experiment are shown, using 2 × 10³ phage and about 108–109 cells per plate. Cells, with an FRT site positioned into either the lacZ or lacY genes as noted, were targeted with λFRT36, a modified λ phage with an FRT site and selectable marker (21).
[b]The average ratio of integration frequencies with or without induction of transcription
[c]n = number of independent experiments.

We claim:

1. A method of introducing exogenous cloned DNA into a bacterial chromosome in which the transposon Tn5 and the FLP recombinase are functional in vivo, comprising the steps of:
   (a) introducing FLP recombination target sites (FRTs) permanently at random locations in a bacterial chromosome using a plasmid vector that contains an FRT within a modified transposon, two selectable markers, and a removable replication origin;
   (b) mapping the introduced FRT;
   (c) cloning exogenous DNA into a plasmid vector comprising two FRT sites, two selectable markers, and a removable replication origin;
   (d) removing the replication origin in the vector of step (c);
   (e) introducing the altered plasmid vector of step (d) into bacterial cells, wherein the bacteria cells comprise a functional FLP recombinase; and
   (f) obtaining targeted integrants.

2. The method of claim 1 wherein the transposon is a Tn5 transposon.

3. The method of claim 1 wherein the bacteria is a gram negative bacteria.

4. The method of claim 2 wherein the bacteria is an *E. coli*.

5. The method of claim 1 wherein the FRT is introduced into the bacterial chromosome on a modified Tn5 transposon.

6. The method of claim 1 wherein FLP recombinase is used in step (d) to remove the origin of replication.

7. The method of claim 1 wherein XbaI and DNA ligase are used in step (d) to remove the origin of replication.

8. The method of claim 1 wherein more than one FRT is introduced into the bacterial chromosome.

9. The method of claim 8 wherein the FRTs do not react with each other.

10. A plasmid comprising:
    a) at least one FRT site;
    b) a nucleic acid sequence encoding a selectable marker located between two outside ends of transposon Tn5; and
    c) a removable replication origin and
    d) a gene for the Tn5 transposase located outside the sequence defined in a) and b).

11. A plasmid comprising:
    a) at least one FRT site;
    b) a nucleic acid sequence encoding a selectable marker located between two outside ends of transposon Tn5; and
    c) a gene for the Tn5 transposase located outside the sequence defined in a) and b),
    wherein the plasmid also comprises:
      i) at least one other FRT site wherein the FRT sites define boundaries of two plasmid segments, segment a and segment b;
      ii) nucleic acid sequences encoding two selectable markers, wherein one marker is in segment a and one marker is in segment b;
      iii) a removable replication origin in segment b; and
      iv) at least one restriction site positioned for use as a cloning site in segment a which leaves both selectable markers intact, wherein the restriction site is part of a polylinker providing at least two restriction sites.

* * * * *